United States Patent
Lee

(10) Patent No.: US 9,025,724 B2
(45) Date of Patent: May 5, 2015

(54) METHOD FOR ANALYZING INTERNAL DENSITY OF MATERIAL BY USING X-RAY COMPUTED TOMOGRAPHY

(75) Inventor: Jae Yeol Lee, Daejeon (KR)

(73) Assignee: Agency for Defense Development, Daejeon (KR)

( * ) Notice: Subject to any disclaimer, the term of this patent is extended or adjusted under 35 U.S.C. 154(b) by 289 days.

(21) Appl. No.: 13/697,220

(22) PCT Filed: May 6, 2011

(86) PCT No.: PCT/KR2011/003370
§ 371 (c)(1),
(2), (4) Date: Jan. 7, 2013

(87) PCT Pub. No.: WO2011/142553
PCT Pub. Date: Nov. 17, 2011

(65) Prior Publication Data
US 2013/0202078 A1  Aug. 8, 2013

(30) Foreign Application Priority Data
May 13, 2010 (KR) .................. 10-2010-0044726

(51) Int. Cl.
*A61B 6/03* (2006.01)
*G01N 23/04* (2006.01)
*G01N 9/24* (2006.01)

(52) U.S. Cl.
CPC ............... *G01N 9/24* (2013.01); *G01N 23/046* (2013.01); *G01N 2223/419* (2013.01)

(58) Field of Classification Search
CPC .......... A61B 6/03; A61B 6/582–6/585; G01N 23/04
USPC ............. 378/4, 6, 10, 21, 51, 54, 86, 89, 56
See application file for complete search history.

(56) References Cited

U.S. PATENT DOCUMENTS

| | | | |
|---|---|---|---|
| 4,613,754 A * | 9/1986 | Vinegar et al. | 250/252.1 |
| 4,873,707 A | 10/1989 | Robertson | |
| 5,673,303 A | 9/1997 | Hangartner | |
| 5,774,520 A | 6/1998 | Bolotin | |

(Continued)

FOREIGN PATENT DOCUMENTS

| | | |
|---|---|---|
| JP | 63-165739 | 7/1988 |
| JP | 11-155852 | 6/1999 |

(Continued)

*Primary Examiner* — Robert Kim
*Assistant Examiner* — David E Smith
(74) *Attorney, Agent, or Firm* — Harness, Dickey & Pierce, P.L.C.

(57) ABSTRACT

Disclosed is a method for analyzing internal density of material by using X-ray computed tomography, comprising the steps of installing a cylinder-shaped jig between an x-ray generator and an x-ray detector, inserting a material to be analyzed and a plurality of standard specimens whose densities are known into the inside of the cylinder-shaped jig, performing X-ray computed tomography while rotating the cylinder-shaped jig through 360°, and calculating the internal density of distribution of the material to be analyzed by using the X-ray intensities shown in the x-ray tomography image. By using the method of the present invention, X-ray tomography image is converted to the image showing the internal density distribution of the material, improving the qualitative decision by naked eye by providing quantitative decision method.

5 Claims, 2 Drawing Sheets

(56) References Cited

U.S. PATENT DOCUMENTS

| | | | |
|---|---|---|---|
| 7,599,468 B2 * | 10/2009 | Zuendorf et al. | 378/38 |
| 2006/0088198 A1 * | 4/2006 | Arnold | 382/131 |
| 2010/0266190 A1 * | 10/2010 | Zagorchev et al. | 382/132 |

FOREIGN PATENT DOCUMENTS

| | | | |
|---|---|---|---|
| JP | 2004-275334 | 10/2004 | |
| JP | 2004275334 A * | 10/2004 | A61B 6/03 |

* cited by examiner

METHOD FOR ANALYZING INTERNAL DENSITY OF MATERIAL BY USING X-RAY COMPUTED TOMOGRAPHY

TECHNICAL FIELD

The present invention relates to a method for analyzing internal density of material by using x-ray computed tomography, and more specifically, to a method for analyzing internal density of material by using x-ray computed tomography by which inside of material can be analyzed quantitatively by using an x-ray tomography image.

BACKGROUND ART

The intensity of x-ray which has transmitted a material is detected by radiating x-ray to the material placed between an x-ray generator and an x-ray detector. By reconstructing, through a computer, the intensities of the x-rays which have been shot while rotating the material, a distribution of x-ray absorption inside the material cross-section can be obtained, which is called x-ray tomography computed tomography.

The x-ray tomography is a typical non-destructive method of analyzing material, the absorption coefficient of the x-ray being known as a function of density of the material. An x-ray tomography image is a result obtained by converting the difference among absorption coefficients to a shaded image, which can be decoded by trained staffs. The method, however, resorts to a qualitative decision through a naked eye, which can include errors due to the experience and subjective feeling of a person and has limitation in its reproducibility.

U.S. Pat. No. 5,774,520 provides method of obtaining clear x-ray tomography image by using a single gamma ray excluding scattering, but just show the density difference as the difference between absorption coefficients failing to provide actual quantitative density distribution.

DISCLOSURE OF INVENTION

Technical Problem

The present invention has been designed to solve the above mentioned problems and aims to provide a method for analyzing internal density of material by using x-ray computed tomography by which inside of material can be analyzed quantitatively by using an x-ray tomography image.

Solution to Problem

In order to obtain the object of the present invention, the method for analyzing internal density of material by using X-ray computed tomography comprises the steps of: a) installing a cylinder-shaped jig between an x-ray generator and an x-ray detector, b) inserting a material to be analyzed and a plurality of standard specimens whose densities are known into the inside of the cylinder-shaped jig, c) performing X-ray computed tomography while rotating the cylinder-shaped jig through 360°, and d) calculating the internal density of distribution of the material to be analyzed by using the X-ray intensities shown in the x-ray tomography image.

The number of standard specimens in step b) is preferably 3-20.

Also the standard specimens preferably have homogeneous internal density.

Also the standard specimens preferably have all different internal densities.

Also preferably, the standard specimens comprise specimens with density higher than the material to be analyzed and specimens with density lower than the material to be analyzed.

In the step d), the calculation of internal density distribution of the material to be analyzed is performed based on the density of the standard specimens and the X-ray intensity in the region of standard specimens present at the X-ray tomography image by using the following formula:

$$D(X) = DM - \left( \frac{\sum_{i=1}^{N}(Ai-AM)(Di-DM)}{\sum_{i=1}^{N}(Ai-AM)^2} \times AM \right) + \left( \frac{\sum_{i=1}^{N}(Ai-AM)(Di-DM)}{\sum_{i=1}^{N}(Ai-AM)^2} \times X \right),$$

where X is an X-ray intensity at one region inside the material to be analyzed, D(X) is the density at the region, Di is the density of each standard specimen, Ai is the average of X-ray intensity at the region of the X-ray tomography image corresponding to the standard specimen, DM is the average of all the Di, AM is the average of all Ai, and N is the number of standard specimens.

Advantageous Effects of Invention

By using the method of the present invention, X-ray tomography image is converted to the image showing the internal density distribution of the material, improving the qualitative decision by naked eye by providing quantitative decision method.

BEST MODE FOR CARRYING OUT THE INVENTION

Now, the present invention will be described in more detail with reference to the attached drawings.

Figure 1:
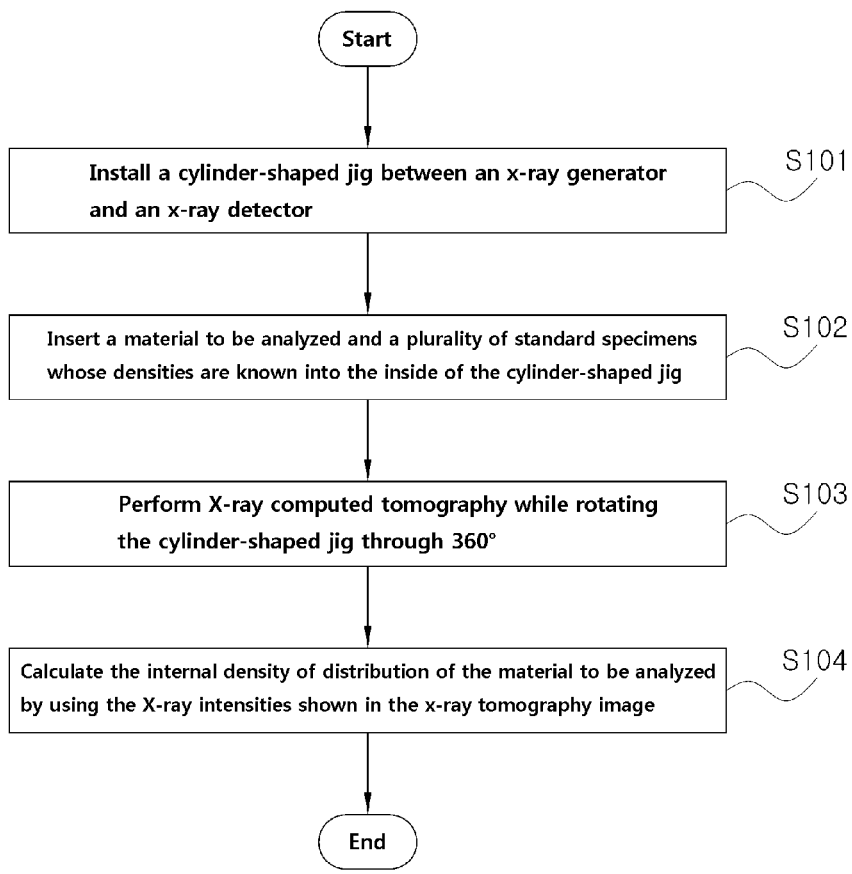
FIG. 1 shows the process of performing the method of the present invention of analyzing the internal density of material by using X-ray tomography.

FIG. 1 shows the process of performing the method of the present invention of analyzing the internal density of material by using X-ray tomography.

Figure 2:
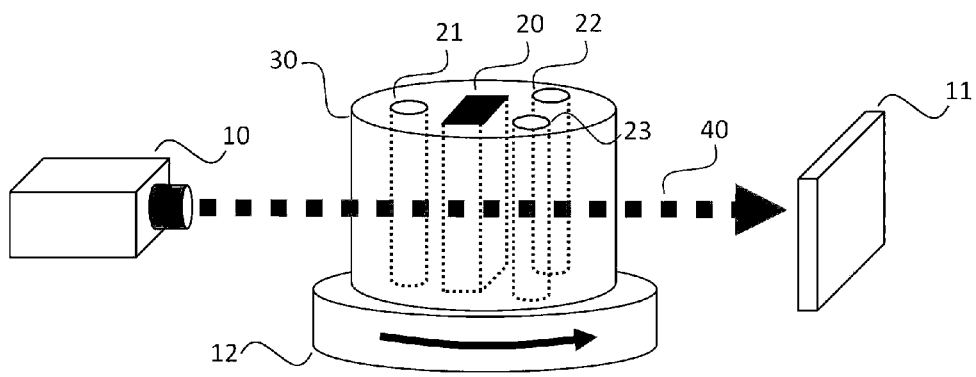
FIG. 2 shows the construction of the apparatus for use in performing the method of the present invention of analyzing the internal density of material by using X-ray tomography.

Referring to FIG. 1, according to the method of the present invention of analyzing the internal density of material by using X-ray tomography, a cylinder-shaped jig 30 is installed between an X-ray generator 10 and an X-ray detector 11, as shown in FIG. 2 (step S101). The jig 30 has the structure into which the material 20 to be analyzed and standard specimens 21, 22, 23 can be inserted, and the outer surface of the jig 30 has preferably cylinder shape without edge since the presence of edge can generate unnecessary noise to the X-ray tomography image due to refraction and diffraction from the edge.

After installing the jig 30, the material 20 to be analyzed and a plurality of standard specimens 21, 22, 23, whose densities are known are inserted into the inside of the cylinder-shaped jig 30 (step S102).

Then, X-ray computed tomography is performed while rotating the cylinder-shaped jig 30 through 360° by rotating the turn table 12 supporting the jig 30 (step S103).

Figure 3:
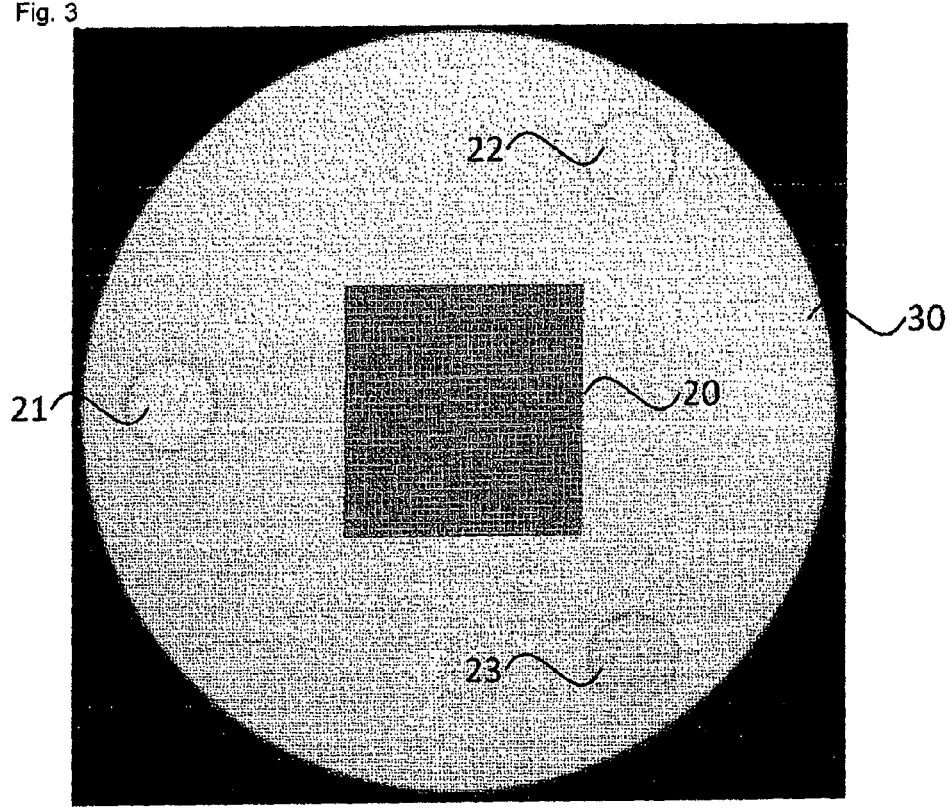
FIG. 3 shows the X-ray tomography image obtained by the method of the present invention of analyzing the internal density of material by using X-ray tomography.

Finally, the internal density of distribution of the material 20 to be analyzed is calculated by using the X-ray intensities shown in the x-ray tomography image as shown in FIG. 3 (step S104).

Here, the number of standard specimens 21, 22, 23 in step S102 is preferably 3-20.

Also the standard specimens 21, 22, 23 preferably have homogeneous internal density.

Also the standard specimens 21, 22, 23 preferably have all different internal densities.

Also preferably, the standard specimens 21, 22, 23 comprise specimens with density higher than the material 20 to be analyzed and specimens with density lower than the material to be analyzed.

Also, in the step S104, the calculation of internal density distribution of the material 20 to be analyzed is performed based on the density of the standard specimens 21, 22, 23 and the X-ray intensity in the region of standard specimens present at the X-ray tomography image by using the following mathematical formula:

$$D(X) = DM - \left( \frac{\sum_{i=1}^{N}(Ai - AM)(Di - DM)}{\sum_{i=1}^{N}(Ai - AM)^2} \times AM \right) + \left( \frac{\sum_{i=1}^{N}(Ai - AM)(Di - DM)}{\sum_{i=1}^{N}(Ai - AM)^2} \times X \right),$$

where X is an X-ray intensity at one region inside the material to be analyzed, D(X) is the density at the region, Di is the density of each standard specimen, Ai is the average of X-ray intensity at the region of the X-ray tomography image corresponding to the standard specimen, DM is the average of all the Di, AM is the average of all Ai, and N is the number of standard specimens.

The above series of processes will now be described in more detail.

The X-ray 40 generated by the X-ray generator 10 passes through the jig 30 containing the material to be analyzed 20 and the standard specimens 21, 22, 23, and reaches the X-ray detector 11. At this stage, the X-ray absorption coefficients depend on the density of the region through which the X-ray 40 passes, and these differences in transmission intensities are recorded on the X-ray detector 11.

The jig 30, the material 20 to be analyzed and the standard specimens 21, 22, 23 rotate through 360° as the turn table 12 is rotated. As the turn table 12 rotates a certain amount of angle, X-ray is radiated again, so that the differences in the intensity of the X-ray resulting from the difference in absorption coefficients are recorded.

FIG. 3 shows the X-ray tomography image of internal cross section of the material obtained by reconstructing the X-ray intensities of the images. At the center of the jig 30 is the image of the material to be analyzed 20, and on the periphery is the image of the standard specimens 21, 22, 23. The standard specimens 21, 22, 23 are provided as a reference for analyzing the density of the material to be analyzed 20, and are not limited to specific materials. In other words, any material including metal, ceramics or plastic can be used, but a single material with homogeneous internal density is preferable. The reason is that the change in the density of the standard specimens 21, 22, 23, which is a basis for the analysis, result in the change in the analysis result of the material to be analyzed 20. Also, the density of each standard specimen 21, 22, 23 should be different, and preferably comprises specimens with density higher than the material 20 to be analyzed and specimens with density lower than the material to be analyzed. The reason is that the reliability in the correlation between the X-ray intensity and density becomes higher as the density of the material 20 to be analyzed is within the density distribution of the standard specimens 21, 22, 23.

The number of standard specimens 21, 22, 23 is variable, but preferably is 3-20. When the number of the standard specimens is less than 3, it is too small for the reference of exact density, and when the number of the standard specimens is more than 20, the time for analysis becomes longer with little increase in accuracy.

The internal density of the material 20 to be analyzed can be calculated quantitatively by using the above mathematical formula, where Di is the density of standard specimens 21, 22, 23, and Ai is the average of X-ray intensity at the region of the X-ray tomography image corresponding to the standard specimen.

Figure 4:
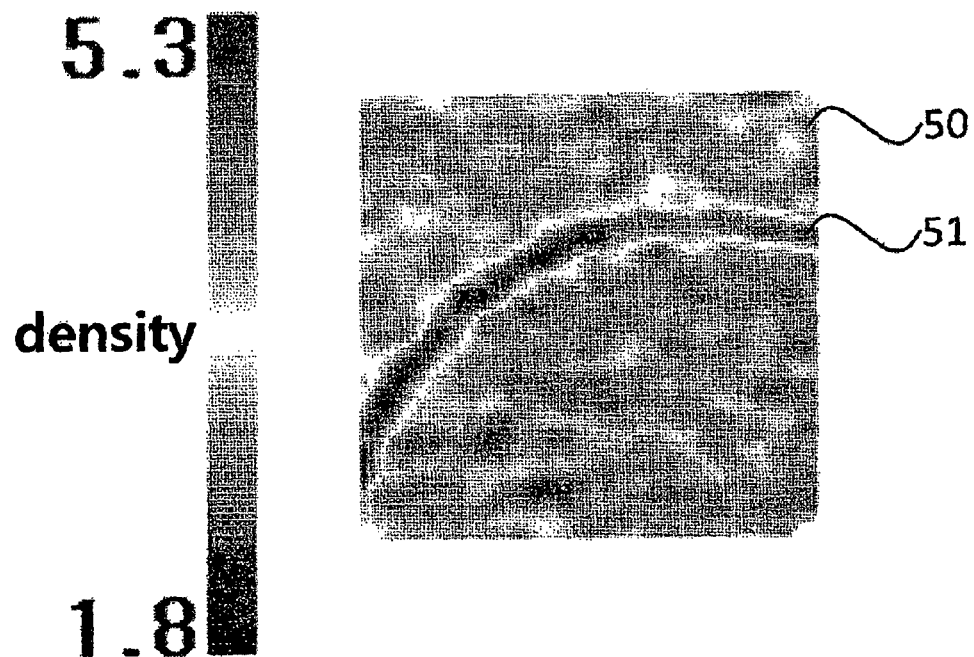
FIG. 4 shows the result of quantitative analysis of the internal density of material obtained by the method of the present invention of analyzing the internal density of material by using X-ray tomography.

FIG. 4 shows the result of quantitative analysis of the internal density D(X) of material obtained by applying the above formula to every region inside the material 20 to be analyzed. In FIG. 4, the internal density of the material 20 to be analyzed is in the range of 5.3-1.8 g/cm².

The region represented by red color is normal region 50 inside the material with high density, and the region represented by blue color is defective region 51 with low density, which results from the crack of the material or generation of air bubbles.

As described above, by using the method of the present invention, X-ray tomography image is converted to the image showing the internal density distribution of the material, improving the qualitative decision by naked eye by providing quantitative decision method.

The present invention has been described in detail with reference to a preferable example. The invention, however, is not limited by the example, and it is obvious that the example can be variously modified by those skilled in the art within the scope of the present invention. Accordingly, the scope of the invention should be interpreted by the claims attached, and all technical ideas which are equivalent to the present invention should be regarded as belonging to the scope of the present invention.

DESCRIPTION OF NUMERALS IN THE DRAWINGS

10 . . . x-ray generator 11 . . . x-ray detector
12 . . . turn table 20 . . . material to be analyzed
21,22,23 . . . standard specimen 30 . . . jig
40 . . . x-ray 50 . . . normal portion inside the material to be analyzed
51 . . . defective portion inside the material to be analyzed

The invention claimed is:

1. A method for analyzing internal density of material by using X-ray computed tomography, comprising the steps of:
   a) installing a cylinder-shaped jig between an x-ray generator and an x-ray detector,
   b) inserting a material to be analyzed and a plurality of standard specimens whose densities are known into the inside of the cylinder-shaped jig,
   c) performing X-ray computed tomography while rotating the cylinder-shaped jig through 360°, and
   d) calculating the internal density of distribution of the material to be analyzed by using the X-ray intensities shown in the x-ray tomography image,
   wherein the calculation of internal density distribution of the material to be analyzed is performed based on the density of the standard specimens and the X-ray intensity in the region of standard specimens present at the X-ray tomography image by using the following formula:

$$D(X) = DM - \left( \frac{\sum_{i=1}^{N}(Ai-AM)(Di-DM)}{\sum_{i=1}^{N}(Ai-AM)^2} \times AM \right) + \left( \frac{\sum_{i=1}^{N}(Ai-AM)(Di-DM)}{\sum_{i=1}^{N}(Ai-AM)^2} \times X \right),$$

where X is an X-ray intensity at one region inside the material to be analyzed, D(X) is the density at the region, Di is the density of each standard specimen, Ai is the average of X-ray intensity at the region of the X-ray tomography image corresponding to the standard specimen, DM is the average of all the Di, AM is the average of all Ai, and N is the number of standard specimens.

2. The method of claim 1, wherein the number of standard specimens is 3-20.

3. The method of claim 1, wherein the standard specimens have homogeneous internal density.

4. The method of claim 1, wherein the standard specimens have all different internal densities.

5. The method of claim 1, wherein the standard specimens comprise specimens with density higher than the material to be analyzed and specimens with density lower than the material to be analyzed.

* * * * *